(12) United States Patent
O'Brien

(10) Patent No.: US 6,483,002 B1
(45) Date of Patent: *Nov. 19, 2002

(54) INTEGRATED FRACTIONAL DISTILLATION FOR ADSORPTIVE SEPARATION PROCESS

(75) Inventor: Dennis E. O'Brien, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/670,159

(22) Filed: Sep. 26, 2000

(51) Int. Cl.[7] .............................. C07C 7/12; B01D 3/00; B01D 3/10; C10G 7/00
(52) U.S. Cl. ...................... 585/826; 585/820; 585/825; 585/828; 585/831; 208/347; 208/350; 208/355; 208/357
(58) Field of Search ................................. 585/831, 820, 585/825, 828, 826; 208/347, 350, 357, 355; 202/158; 203/42; 196/111

(56) References Cited

U.S. PATENT DOCUMENTS

| | | | |
|---|---|---|---|
| 2,471,134 A | 5/1949 | Wright | 196/111 |
| 3,201,491 A | 8/1965 | Stine et al. | 260/676 |
| 3,205,166 A | 9/1965 | Ludlow et al. | 208/310 |
| 3,510,423 A | 5/1970 | Neuzil et al. | 208/310 |
| 4,006,197 A | 2/1977 | Bieser | 260/676 MS |
| 4,036,745 A | 7/1977 | Broughton | 208/310 |
| 4,230,533 A | 10/1980 | Giroux | 203/1 |
| 5,177,295 A | 1/1993 | Oroskar et al. | 585/805 |
| 5,300,715 A | 4/1994 | Vora | 585/254 |
| 6,348,637 B1 * | 2/2002 | Harris | |

OTHER PUBLICATIONS

Rudd, H. "Thermal Coupling for Energy Efficiency" *Supplement to The Chemical Engineer* p. s44–s15 Aug. 27, 1992.
Schulz, R.C. (et al.) "Lab Production" Poster Session at the 2nd World Conference on Detergents Montreux, Switzerland Oct. 5–10, 1986.

* cited by examiner

Primary Examiner—Walter D. Griffin
Assistant Examiner—Tam M. Nguyen
(74) Attorney, Agent, or Firm—John G. Tolomei; James C. Paschall

(57) ABSTRACT

Construction and operational costs of simulated moving bed adsorptive separation process units are reduced by recovering desorbent from both the extract and raffinate streams of the process in a single column. Both streams are fractionated to recover desorbent, which is removed at one end of a dividing wall column, while separate extract and raffinate products are removed from the other end of the column.

11 Claims, 1 Drawing Sheet

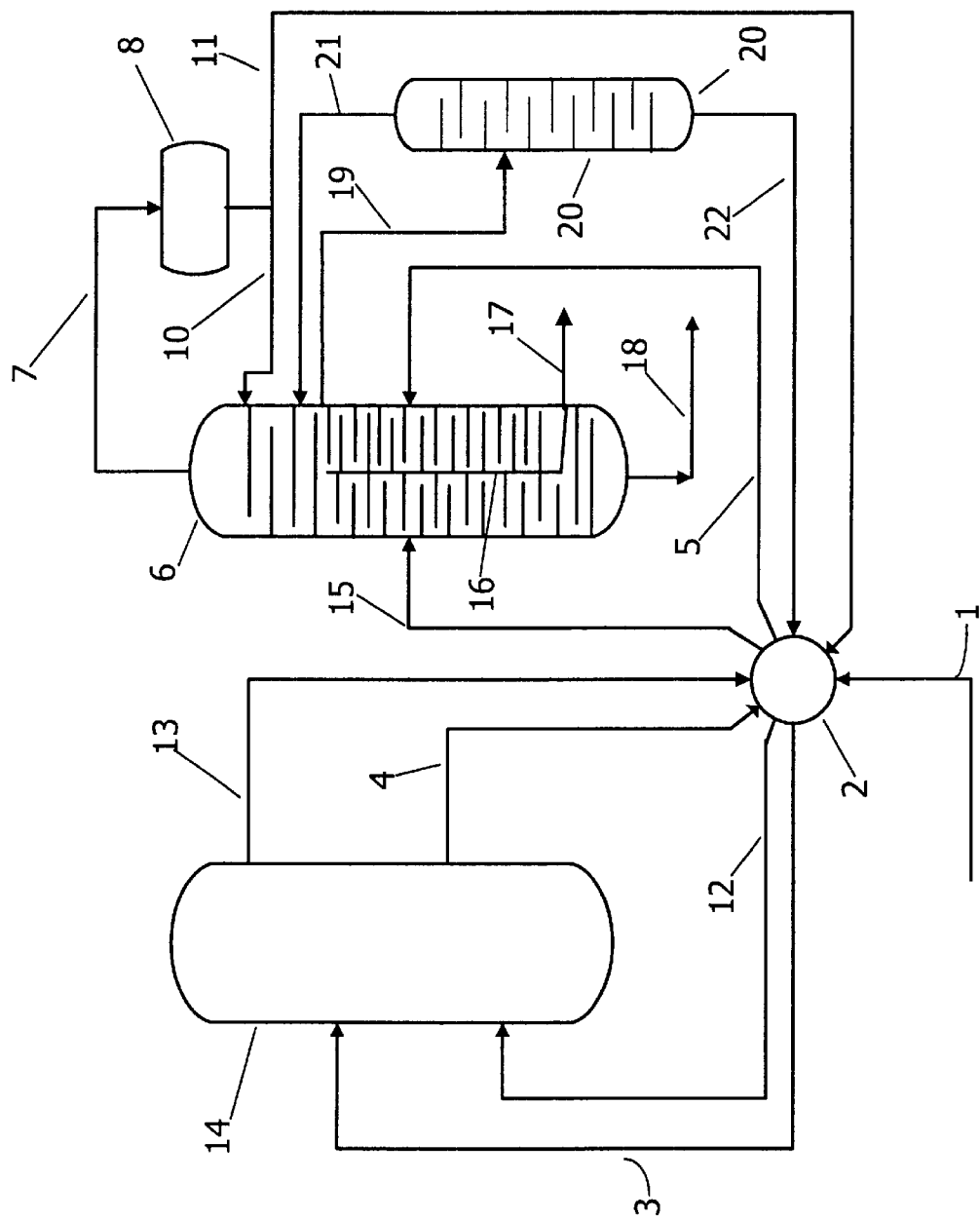

INTEGRATED FRACTIONAL DISTILLATION FOR ADSORPTIVE SEPARATION PROCESS

FIELD OF THE INVENTION

The invention relates to a continuous adsorptive separation process used to separate chemical compounds such as petrochemicals. The invention specifically relates to an innovative fractional distillation method which reduces the cost of recovering desorbent from the effluent streams of a continuous adsorptive separation process.

BACKGROUND OF THE INVENTION

In many commercially important petrochemical and petroleum industry processes it is desired to separate closely boiling chemical compounds or to perform a separation of chemical compounds by structural class. It is very difficult or impossible to do this by conventional fractional distillation due to the requirement of numerous columns or excessive amounts of energy. The relevant industries have responded to this problem by utilizing other separatory methods which are capable of performing a separation based upon chemical structure or characteristics. Adsorptive separation is such a method and is widely used to perform these separations.

In the practice of adsorptive separation a feed mixture comprising two or more compounds of different skeletal structure is passed through one or more beds of an adsorbent which selectively adsorbs a compound of one skeletal structure while permitting other components of the feed stream to pass through the adsorption zone in an unchanged condition. The flow of the feed through the adsorbent bed is stopped and the adsorption zone is then flushed to remove nonadsorbed materials surrounding the adsorbent. Thereafter the desired compound is desorbed from the adsorbent by passing a desorbent stream through the adsorbent bed. The desorbent material is commonly also used to flush nonadsorbed materials from the void spaces around and within the adsorbent. This could be performed in a single large bed of adsorbent or in several parallel beds on a swing bed basis. However, it has been found that simulated moving bed adsorptive separation provides several advantages such as high purity and recovery. Therefore, many commercial scale petrochemical separations especially for specific paraffins and xylenes are performed using simulated countercurrent moving bed (SMB) technology.

RELATED ART

A description of the use of simulated moving bed (SMB) adsorptive separation to recover paraffins from a kerosene boiling range petroleum fraction is provided in the contents of a presentation made by R. C. Schulz et al. at the 2nd World Conference on Detergents in Montreux, Switzerland on Oct. 5–10, 1986. This shows several incidental steps in the process such as fractionation and hydrotreating. A more detailed overall flow scheme for the production of olefins from the kerosene derived paraffins is presented in U.S. Pat. No. 5,300,715 issued to B. V. Vora.

Several economic advantages are derived from the continuous, as compared to batch-wise, operation of a large scale adsorptive separation processes. Recognition of this has driven the development of simulated moving bed (SMB) adsorptive separation processes. These processes typically employ a rotary valve and a plurality of lines to simulate the countercurrent movement of an adsorbent bed through adsorption and desorption zones. This is depicted, for instance, in U.S. Pat. No. 3,205,166 to D. M. Ludlow, et al. and U.S. Pat. No. 3,201,491 to L. O. Stine et al.

U.S. Pat. No. 3,510,423 to R. W. Neuzil et al. provides a depiction of the customary manner of handling the raffinate and extract streams removed from an SMB process, with the desorbent being recovered, combined and recycled to the adsorption zone. U.S. Pat. No. 4,036,745 describes the use of dual desorbent components with a single adsorption zone to provide a higher purity paraffin extract. U.S. Pat. No. 4,006,197 to H. J. Bieser extends this teaching on desorbent recycling to three component desorbent mixtures.

U.S. Pat. No. 5,177,295 issued to A. R. Oroskar et al. describes the fractionation of a "heavy" desorbent used in the recovery of paraxylene from a mixture of aromatic hydrocarbons.

The dividing wall or Petyluk configuration for fractionation columns was initially introduced some 50 years ago by Petyluk et al. A recent commercialization of a fractionation column employing this technique prompted more recent investigations as described in the article appearing at page 14 of a supplement to *The Chemical Engineer*, Aug. 27, 1992.

The use of dividing wall columns in the separation of hydrocarbons is also described in the patent literature. For instance, U.S. Pat. No. 2,471,134 issued to R. O. Wright describes the use of a dividing wall column in the separation of light hydrocarbons ranging from methane to butane. U.S. Pat. No. 4,230,533 issued to V. A. Giroux describes a control system for a dividing wall column and illustrates the use of the control system in the separation of aromatics comprising benzene, toluene and orthoxylene.

BRIEF SUMMARY OF THE INVENTION

The invention is an improved simulated moving bed adsorptive separation process characterized by the used of an integrated fractional distillation column to recover both the extract and raffinate products of the adsorptive separation and the desorbent in a single fractionation column. A portion of the column is divided into parallel fractionation zones with one receiving the raffinate stream and the other receiving the extract stream of the adsorptive separation zone. The desorbent in these streams is rejected into a common portion of the column for further purification. This reduces the capital and operating costs of the required separation and thus of the adsorption process.

One broad embodiment of the invention may be characterized as a simulated moving bed adsorptive separation process which comprises passing a feed stream comprising a first and a second chemical compound into an adsorption zone comprising a bed of a selective adsorbent maintained at adsorption promoting conditions under which the first chemical compound is selectively retained on a quantity of the selective adsorbent, thus forming a raffinate stream comprising the second chemical compound and a desorbent compound formerly present in the quantity-of the selective adsorbent; passing a desorbent into contact with said quantity of the selective adsorbent which has retained the first chemical compound under desorption promoting conditions to yield an extract stream comprising the first chemical compound and the desorbent compound; passing the extract stream into a fractionation column operated at fractionation conditions and divided into at least a first and a second vertical fractionation zones, with each zone having an upper and a lower end located within the fractionation column, with the first and second fractionation zones being in open communication at either their upper or their lower ends at a first end of the column and with the extract stream entering the fractionation column at an intermediate point of the first fractionation zone; passing the raffinate stream into an intermediate point of the second fractionation zone of the fractionation column; removing an extract product stream from a first end of the first fractionation zone, said first end not being in communication with the second fractionation zone and being located at the second end of the column; removing a raffinate product stream from a first end of the second fractionation zone, said first end not being in communication with the first fractionation zone; and, removing a desorbent stream comprising the desorbent compound from the first end of the fractionation column.

BRIEF DESCRIPTION OF THE DRAWING

The Drawing is a highly simplified process flow diagram showing the extract and raffinate streams removed from the adsorbent chamber 14 being passed into different fractionation zones of a single product recovery column 6.

PREFERRED EMBODIMENTS AND DETAILED DESCRIPTION

In many commercially important petrochemical and petroleum industry processes it is desired to separate closely boiling chemical compounds or to perform a separation of chemical compounds by structural class. Examples of this are the recovery of normal paraffins from petroleum kerosene fractions for use in the production of detergents and the recovery of paraxylene from a mixture of $C_8$ aromatics in the production of polyesters and other plastics. Metaxylene is also recovered by adsorptive separation from xylene feed mixtures. The separation of high octane hydrocarbons from a naphtha boiling range petroleum fraction and the recovery of olefins from a mixture of paraffins and olefins are other examples of situations in which the close volatility of the compounds or the overlap in boiling points across a broad boiling range of compounds makes the use of fractional distillation impractical. For instance in the case of the recovery of normal paraffins referred to above it is often desired to recover paraffins having a range of carbon numbers extending from about $C_9$ to $C_{12}$. This would require multiple fractional distillation columns. The resulting capital and operating costs make this approach economically unattractive.

The relevant industries have responded to this problem by utilizing other separatory methods which are capable of performing a separation based upon chemical structure or characteristics. Adsorptive separation is such a method and is widely used to perform the separations mentioned above. In adsorptive separation one or more compounds are selectively retained upon an adsorbent and then released by the application of a driving force for the desorption step. In the subject process this driving force is provided by contacting the loaded adsorbent with a desorbent compound. Therefore the adsorbent must be continuously cycled between exposure to the feed stream and a stream comprising the desorbent. As described below this forms at least two effluent streams; the raffinate stream which contains unadsorbed compounds and the extract stream containing the desired adsorbed compounds. Both streams also comprise the desorbent compound.

It is an objective of the subject invention to provide a more economical process for recovering the desorbent compound from these two streams produced during adsorptive separation. It is a specific objective of the subject invention to provide an improved simulated moving bed adsorptive separation process having reduced capital costs. These objectives are achieved by reducing the number of fractionation columns required to recover the desorbent from the extract and desorbent. A single integrated column containing parallel fractionation zones in a single column is employed instead of individual columns. Each fractionation zone occupies only a portion of the cross-section of the column, and both zones are in open communication at one end with a larger area undivided section of the column. This open communication may be at either the top or bottom end of the fractionation zones depending on whether the desorbent has a lower or higher boiling point than the raffinate and extract components of the feed.

The overall operation of the subject invention may be discerned by reference to the Drawing. The Drawing illustrates a simulated moving bed adsorptive separation process having a single adsorbent chamber 14 and a single fractional distillation column 6. For purposes of description it is assumed that the process is being employed to separate a feed stream of line 1 comprising a mixture of several $C_8$ aromatic hydrocarbons including paraxylene, and normally also comprising metaxylene, orthoxylene and ethylbenzene. The very close volatilities of these compounds makes it impractical to separate them on a commercial scale by fractional distillation. Therefore the predominant commercial separatory techniques are crystallization and adsorptive separation. In the process depicted in the Drawing the feed stream of line 1 is passed into a rotary valve 2. This rotary valve has a number of ports corresponding to the number of adsorption chamber process streams plus a "bed line" for each sub bed of adsorbent located in the one or more adsorbent chambers used in the process. As the adsorbent chamber(s) may contain from about 8 to about 24 adsorbent sub beds, there are a large number of bed lines involved in the process. For simplicity only those bed lines in use at the moment in time being depicted are shown on the drawing.

The rotary valve 2 directs the feed stream into bed line 3 which carries it to the adsorbent chamber 14. The feed stream enters into the adsorbent chamber at a boundary between two of the sub beds and is distributed across the cross-section of the chamber. It then flows downward through several sub-beds of adsorbent containing particles. The adsorbent selectively retains one compound or structural class of compound, which in this instance is paraxylene. The other components of the feed stream continue to flow downward and are removed from the adsorbent chamber in the raffinate stream carried by line 4. The raffinate stream will also comprise a varying amount of desorbent compound(s) flushed from the inter-particle void volume and removed from the adsorbent itself. This desorbent is present in the bed prior to the adsorption step due to the performance of the desorption step.

The raffinate stream enters the rotary valve 2 and is then directed into line 5. Line 5 carries the raffinate stream to a vertical fractionation zone shown occupying portions of the right hand side of the fractional distillation column 6. This fractionation zone contains about 35–40 fractionation trays and is separated from the other fractionation zone in the column by a substantially fluid tight vertical wall 16. The vertical wall is not necessarily centered in the column. The vertical wall 16 divides a large portion of the column 6 into two parallel fractionation zones. The two zones are isolated from each other for the height of this wall and also at the bottom of the wall. This seal at the bottom of the first zone distinguishes the column from a true dividing wall column. Thus there is no direct vapor or liquid flow between the two fractionation zones. The upper end of the fractionation zone receiving the raffinate stream of line 5 is however open to the internal volume of the column 6. Thus vapor and liquid can freely move between these two portions of the column. This opening of the top of each fractionation zone into a larger fractionation zone allows vapor from both parallel zones to flow upward. The two smaller zones are thus described as being in open communication with each other and this larger zone at this point in the column. Liquid flow downward may or may not be regulated between the zones. Both of the fractionation zones have independent reboiling means not shown. During operation, the raffinate stream entering the first fractionation zone is separated with the more volatile desorbent component(s) moving upward out of the fractionation zone and emerging into the upper portion of the column 6. The less volatile raffinate components, e.g. meta and ortho xylene, of the feed stream are concentrated into a bottoms stream removed from the first fractionation zone via line 17.

Simultaneously a stream of desorbent is passed into the adsorbent chamber 14 via line 12. As the desorbent moves downward through the adsorbent it removes paraxylene from the adsorbent in a section of the chamber used as the desorption zone. This creates a mixture of paraxylene and desorbent which flows through the section of the adsorbent chamber functioning as the desorption zone. This material is removed from the bottom of the chamber 14 and returned to the top of the chamber via a line not shown referred to in the art as the pump around line. It flows through more adsorbent at the top of the chamber and is then removed from the adsorbent chamber 14 via line 13 as the extract stream passed into the rotary valve 2. The rotary valve directs the extract stream of line 13 into line 15. Line 15 delivers the extract stream into a second vertical fractionation zone occupying a large portion of the left hand side of column 6. The less volatile extract component, para-xylene, moves downward through the second fractionation zone and is removed from column 6 via line 18. As with the first fractionation zone, the upper end of the second zone is in open communication with the upper section of the column 6, which contains additional fractionation trays extending across the entire column cross-section.

The desorbent compound(s) present in the extract stream of line 15 is driven upward in the second fractionation zone and enters the top of the column 6. The top of the column is a purification zone which is not intended for separation of extract or raffinate compounds from the desorbent. This section can be used for a separation of different desorbent components when a multi-component desorbent stream is employed. A vapor stream comprising the desorbent component(s) is removed from the top of column 6. via line 7 and passed through an overhead condenser not shown to form liquid delivered to the receiver 8. A stream of liquid phase desorbent is removed from the receiver and divided into a first portion which is returned to the top of the fractionation column 6 via line 10 as reflux and a second portion which is passed through line 11 to the rotary valve 2.

The preceding description of the Drawing has been in terms of the use of a single component desorbent. The use of multiple component desorbents is, however, very important in some separations and is especially preferred in the separation of normal paraffins from a mixture of various other types of hydrocarbons. The use of a mixture of a normal paraffin and an isoparaffin, both several carbon numbers lighter than the feed, is practiced commercially. A representative dual component mixture for the recovery of $C_{10}$–$C_{15}$ normal paraffins comprises normal pentane and iso-octane. When the subject invention is applied to a process using a dual component desorbent the integrated column can also produce a sidecut stream removed: via line 19 and passed into the desorbent splitter column 20. The sidecut will contain all the desorbent components e.g. normal pentane and iso-octane. This sidecut stream is fed into an intermediate point in the column 20, which is maintained at fractional distillation conditions which promote the separation of the lightest of the entering hydrocarbons into an overhead vapor stream removed in line 21. This overhead vapor is enriched in n-pentane and returned to an upper intermediate point of the main column 6 via line 21. The remaining iso-octane is concentrated into the net bottoms stream removed in line 22 and passed to the rotary valve 2. In this way streams rich in the separate desorbent components are delivered to the rotary valve and may be employed at different points in the desorption operation. For instance, a "zone flush" material or a bed-line flush material used in the process can be rich in iso-octane while the main desorbent stream used to remove normal paraffins from the adsorbent can be rich in n-pentane. As used herein the term "rich" is intended to indicate a concentration of the indicated compound or class of compounds greater than 50 and preferably greater than 75 mol percent.

A preferred embodiment of the invention may, therefore, be characterized as a simulated moving bed adsorptive separation process which comprises passing a feed stream comprising a first and a second chemical compound into an adsorption zone comprising a bed of a selective adsorbent maintained at adsorption promoting conditions under which the first chemical compound is selectively retained on a quantity of the selective adsorbent, thus forming a raffinate stream comprising the second chemical compound and a desorbent compound formerly present in the quantity of the selective adsorbent; passing a first desorbent stream comprising a first and a second desorbent compound into contact with said quantity of the selective adsorbent which has retained the first chemical compound under desorption promoting conditions to yield an extract stream comprising the first chemical compound and the first and second desorbent compounds; passing the extract stream into an intermediate point of a first vertical fractionation zone of a fractionation column operated at fractionation conditions and divided into at least the first fractionation zone and a substantially parallel second fractionation zone, with each zone having an upper and a lower end located within the fractionation column, with the first and second fractionation zones being in open communication at their upper end, with the fractionation column also containing an undivided fractionation section extending from the point of open communication between the first and second fractionation zones to an upper first end of the fractionation column; passing the raffinate stream into an intermediate point of the second fractionation zone of the fractionation column; removing an extract product stream from the lower end of the first fractionation zone, said first end not being in communication with the second fractionation zone; removing a raffinate product stream from a lower end of the second fractionation zone, said lower end not being in communication with the first fractionation zone; removing a second desorbent stream comprising the first desorbent compound from the first end of the fractionation column; and, removing a third desorbent stream comprising the second desorbent compound from the an intermediate point in the fractionation column located between the first end of the fractionation column and the upper end of the first fractionation zone.

Operating conditions for adsorption include, in general, a temperature range of from about 20 to about 250° C., with from about 60 to about 200° C. often being preferred.

Adsorption conditions also preferably include a pressure sufficient to maintain the process fluids in liquid phase; which may be from about atmospheric to 600 psig. Desorption conditions generally include the same temperatures and pressure as used for adsorption conditions. It is generally preferred that an SMB process is operated with an A:F flow rate through the adsorption zone in the broad range of about 1:1 to 5:1.0 where A is the volume rate of "circulation" of selective pore volume and F is the feed flow rate. The practice of the subject invention requires no significant variation in operating conditions, adsorbent or desorbent composition within the adsorbent chambers. That is the adsorbent preferably remains at the same temperature throughout the process.

Although much of the description herein is set in terms of use of the invention in an SMB process, the invention is believe applicable to other modes of performing adsorptive separation such as a swing bed system employing one or more separate beds of adsorbent. The real limit to the application of the process is that the process produces two streams both comprising a single compound or group of compounds which it is desired to recover by fractionation.

Another variation in the performance of the process is the replacement of the rotary valve with a manifold system of .valves. Such systems have been described in the art e.g. U.S. Pat. No. 4,434,051, and become more practical as the number of sub-beds of adsorbent decreases. Further variation is possible concerning which of the two streams enters which fractionation zone, which is set primarily by practical engineering considerations.

Yet another variation which departs from the depiction in the Drawing is the instance of a separation in which the desorbent has a higher boiling point than the raffinate and extract components. In this case, the desorbent is removed from the bottom of the fractionation column and both.of the parallel fractionation zones would be open at the bottom and in communication with the larger section from which the desorbent is withdrawn. One of the fractionation zones is sealed at its upper end, and product removed there. The use of "heavy" desorbents, that is desorbents having higher boiling points than the raffinate or extract components of the feed, in the separation of paraxylene is described in U.S. Pat. Nos. 5,107,062; 5,057,643 and 5,012,038. The fractionation of a heavy desorbent from the extract and raffinate is shown in previously cited U.S. Pat. No. 5,177,295.

As different separations are performed in the two parallel separation zones the mechanical details and equipment in the two zones may differ. For instance, they may contain different types of fractionation trays, trays of the same type-but at different spacing or one fractionation zone may contain or be augmented by structured packing.

The success of a particular adsorptive separation is determined by many factors. Predominant in these factors are the composition of the adsorbent (stationary phase) and desorbent (mobile phase) employed in the process. The remaining factors are basically related to process conditions.

The subject process is not believed to be limited to use with any particular form of adsorbent. The adsorbents employed in the process preferably comprise a molecular sieve such as a type A, X or Y zeolite or silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," *Nature*, Vol. 271, Feb. 9, 1978 which is incorporated herein by reference for its description and characterization of silicalite.

Silicalite is a hydrophobic crystalline silica molecular sieve having intersecting bent-orthogonal channels formed with two cross-sectional geometries, 6 Å circular and 5.1–5.7 Å elliptical on the major axis. A wide number of adsorbents are known and a starting molecular sieve is often treated by ion or steaming etc to adjust its adsorptive properties. Adsorbents based upon zeolites X and Y are described in more detail in U.S. Pat. Nos. 3,663,638; 3,626,020 and 3,997,620.

The active component of the adsorbents is normally used in the form of particle agglomerates having high physical strength and attrition resistance. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica are generally used as binders. The active molecular sieve component of the adsorbents will ordinarily be in the form of small crystals present in the adsorbent particles in amounts ranging from about 75 to about 98-wt. % of the particle based on volatile-free composition. Volatile-free compositions are generally determined after the adsorbent has been calcined at 900° C. in order to drive off all volatile matter.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0% and preferably within the range of from 0 to 4.0 wt. %.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which insures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials :should be readily available and reasonable in cost.

As indicated above, the desorbent may be a mixture of two or more compounds. For instance a preferred desorbent for the separation of normal $C_9$–$C_{11}$ paraffins from kerosene comprises a mixture of a normal paraffin and a cycloparaffin (naphthene). A mixture in which the normal and cycloparaffins have the same carbon number is highly preferred, with carbon numbers of the desorbent compounds being in the general range of 5 to 8. The preferred normal paraffin is n-hexane, and the desorbent may range from 0 to 100% normal paraffin. The desorbent may also be 100% cycloparaffin.

Further details on equipment and techniques for using in an SMB process may be found in U.S. Pat. Nos. 3,208,833; 3,214,247; 3,392,113; 3,455,815; 3,523,762; 3,617,504; 4,006,197; 4,133,842; and 4,434,051. A different type of simulated moving bed operation which can be performed using similar equipment, adsorbent and conditions but which simulates cocurrent flow of the adsorbent and liquid in the adsorption chambers is described in U.S. Pat. Nos. 4,402,832 and 4,498,991. A more thorough explanation of simulated moving bed processes is given in the Adsorptive Separation section of the Kirk-Othmer Encyclopedia of Chemical Technology at page 563.

U.S. Pat. No. 4,992,618 issued to S. Kulprathipanja describes the use of a "prepulse" of a desorbent component in an SMB process recovering normal paraffins. The prepulse is intended to improve the recovery of the extract normal paraffins across the carbon number range of the feed. The prepulse enters the adsorbent chamber at a point before (downstream) of the feed injection point. A related SMB processing technique is the use of "zone flush." The zone flush forms a buffer zone between the feed and extract bed lines to keep the desorbent e.g. normal pentane, from entering the adsorption zone. While the use of a zone flush requires a more complicated, and thus more costly rotary valve, the use of zone flush is preferred in the adsorption zones when high purity extract product are desired. In practice, a quantity of the mixed component desorbent recovered overhead from the extract and/or raffinate columns is passed into a separate splitter column. A high purity stream of the lower strength component of the mixed component desorbent is recovered and used as the zone flush stream. Further information on the use of dual component desorbents and on techniques to improve product purity such as the use of flush streams may-be obtained from U.S. Pat. Nos. 3,201,491; 3,274,099; 3,715,409; 4,006,197 and 4,036,745 which are incorporated herein by reference for their teaching on these aspects of SMB technology.

SMB Technology has been applied to a wide variety of chemicals in addition to those described above. For instance, U.S. Pat. No. 4,467,126 describes the recovery of a di-substituted benzene such as a nitrotoluene isomer. The separation of 2,6 di methyl naphthalene is described in U.S. Pat. No. 5,004,853 and 2,7 di isopropylnaphthalene in U.S. Pat. No. 5,012,039. SMB technology has been extended to the separation of sugars, to the separation of chiral compounds and to more complicated organics such as fatty acids and triglycerides as described in U.S. Pat. No. 5,225,580. The separation of fatty acids is described in U.S. Pat. Nos. 4,404,145; 4,770,819; 5,171,870 and 5,179,219. It is believed the subject process can be applied to any SMB process requiring desorbent recovery. This includes the recovery of normal paraffins or slightly branched paraffins for use in the manufacture of detergents by alkylation or by conversion to alcohols or other compounds as described in patent publication WO 00/12451 of Mar. 9, 2000.

For purposes of this invention, various: terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process. containing, respectively, an extract component and a raffinate component in higher concentrations than those found in the extract stream and the raffinate stream withdrawn from adsorbent chamber. The extract stream may be rich in the desired compound or may only contain an increased concentration. The term "rich" is intended to indicate a concentration of the indicated compound or class of compounds greater than 50 mole percent.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a following mixture of desorbent and undesired components of the feed stream. The liquid flow through Zone IV prevents contamination of Zone III by Zone I liquid by flow cocurrent to the simulated motion of the adsorbent from Zone III toward Zone I. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

What is claimed:

1. A simulated moving bed adsorptive separation process which comprises:
   a.) passing a feed stream comprising a first and a second chemical compound into an adsorption zone comprising a bed of a selective adsorbent maintained at adsorption promoting conditions under which the first chemical compound is selectively retained on a quantity of the selective adsorbent, thus forming a raffinate stream comprising the second chemical compound and a desorbent compound formerly present in the quantity of the selective adsorbent;
   b.) passing a desorbent into contact with said quantity of the selective adsorbent which has retained the first chemical compound under desorption promoting conditions to yield an extract stream comprising the first chemical compound and the desorbent compound;
   c.) passing the extract stream into a fractionation column operated at fractionation conditions and divided into at least a first and a second vertical fractionation zones, with each zone having an upper and a lower end located within the fractionation column, with the first and second fractionation zones being in open communication at either their upper or their lower ends at a first end of the column and with the extract stream entering the fractionation column at an intermediate point of the first fractionation zone;
   d.) passing the raffinate stream into an intermediate point of the second fractionation zone of the fractionation column;
   e.) removing an extract product stream from a first end of the first fractionation zone, said first end not being in communication with the second fractionation zone and being located at the second end of the column;
   f.) removing a raffinate product stream from a first end of the second fractionation zone, said first end not being in communication with the first fractionation zone; and,
   g.) removing a desorbent stream comprising the desorbent compound from the first end of the fractionation column.

2. The process of claim 1 wherein an undivided section of the fractionation column is located in the upper half of the fractionation column, and the desorbent stream is removed from the upper end of the fractionation column.

3. The process of claim 1 wherein an undivided section of the fractionation column is located in the lower half of the fractionation column, and the desorbent stream is removed from the lower end of the fractionation column.

4. The process of claim 1 wherein the first and second chemical compounds are paraffinic hydrocarbons.

5. The process of claim 1 wherein the first and second chemical compounds are aromatic hydrocarbons.

6. A simulated moving bed adsorptive separation process which comprises:
   a.) passing a feed stream comprising a first and a second chemical compound into an adsorption zone comprising a bed of a selective adsorbent maintained at adsorption promoting conditions under which the first chemical compound is selectively retained on a quantity of the selective adsorbent, thus forming a raffinate stream comprising the second chemical compound and a desorbent compound formerly present in the quantity of the selective adsorbent;
   b.) passing a desorbent into contact with said quantity of the selective adsorbent which has retained the first chemical compound under desorption promoting conditions to yield an extract stream comprising the first chemical compound and the desorbent compound;
   c.) passing the extract stream into a fractionation column operated at fractionation conditions and divided into at least a first and a second vertical fractionation zones, with each zone having an upper and a lower end located within the fractionation column, with the first and second fractionation zones being in open communication at either their upper or lower ends, with the fractionation column also containing an undivided fractionation section extending from the point of open communication between the first and second fractionation zones to a first end of the fractionation column, with the extract stream entering at an intermediate point of the first fractionation zone;
   d.) passing the raffinate stream into an intermediate point of the second fractionation zone of the fractionation column;
   e.) removing an extract product stream from the first end of the first fractionation zone, said first end not being in communication with the second fractionation zone;
   f.) removing a raffinate product stream from a first end of the second fractionation zone, said first end not being in communication with the first fractionation zone or the first end of the column; and,
   g.) removing a desorbent stream comprising the desorbent compound from the first end of the fractionation column.

7. The process of claim 6 wherein the first chemical compound is a normal paraffin.

8. The process of claim 6 wherein the first chemical compound is an olefin.

9. A simulated moving bed adsorptive separation process which comprises:

a.) passing a feed stream comprising a first and a second chemical compound into an adsorption zone comprising a bed of a selective adsorbent maintained at adsorption promoting conditions under which the first chemical compound is selectively retained on a quantity of the selective adsorbent, thus forming a raffinate stream comprising the second chemical compound and a desorbent compound formerly present in the quantity of the selective adsorbent;

b.) passing a first desorbent stream comprising a first and a second desorbent compound into contact with said quantity of the selective adsorbent which has retained the first chemical compound under desorption promoting conditions to yield an extract stream comprising the first chemical compound and the first and second desorbent compounds;

c.) passing the extract stream into an intermediate point of a first vertical fractionation zone of a fractionation column operated at fractionation conditions and divided into at least the first fractionation zone and a substantially parallel second fractionation zone, with each zone having an upper and a lower end located within the fractionation column, with the first and second fractionation zones being in open communication at their upper end, with the fractionation column also containing an undivided fractionation section extending from the point of open communication between the first and second fractionation zones to an upper first end of the fractionation column;

d.) passing the raffinate stream into an intermediate point of the second fractionation zone of the fractionation column;

e.) removing an extract product stream from the lower end of the first fractionation zone, said first end not being in communication with the second fractionation zone;

f.) removing a raffinate product stream from a lower end of the second fractionation zone, said lower end not being in communication with the first fractionation zone;

g.) removing a second desorbent stream comprising the first desorbent compound from the first end of the fractionation column; and, h.) removing a third desorbent stream comprising the second desorbent compound from the an intermediate point in the fractionation column located between the first end of the fractionation column and the upper end of the first fractionation zone.

10. The process of claim 9 wherein the first chemical compound is a xylene.

11. The process of claim 9 wherein the first chemical compound is metaxylene.

* * * * *